US007692785B2

(12) United States Patent
Sutherland et al.

(10) Patent No.: US 7,692,785 B2
(45) Date of Patent: Apr. 6, 2010

(54) SYSTEM AND METHOD FOR OPTICAL POWER MANAGEMENT

(75) Inventors: Willam Scott Sutherland, Haverhill, MA (US); Anis Zribi, Rexford, NY (US); Long Que, Rexford, NY (US); Glenn Scott Claydon, Wynantskill, NY (US); Stacey Joy Kennerly, Albany, NY (US); Ayan Banerjee, Bangalore (IN); Shivappa Ningappa Goravar, Karnataka (IN); Shankar Chandrasekaran, Tamil Nadu (IN); David Cecil Hays, Niskayuna, NY (US); Victor Samper, Munich (DE); Dirk Lange, Munich (DE); Marko Baller, Munich (DE); Min-Yi Shih, Carson City, NV (US); Sandip Maity, Karnataka (IN)

(73) Assignee: General Electric Company, Niskayuna, NY (US)

( * ) Notice: Subject to any disclaimer, the term of this patent is extended or adjusted under 35 U.S.C. 154(b) by 200 days.

(21) Appl. No.: 11/693,277

(22) Filed: Mar. 29, 2007

(65) Prior Publication Data
US 2008/0239306 A1 Oct. 2, 2008

(51) Int. Cl.
*G01J 3/44* (2006.01)
(52) U.S. Cl. .................................... 356/301
(58) Field of Classification Search ................ 356/311, 356/318, 301, 27; 359/196; 372/20, 33, 372/34, 29.014, 29.021
See application file for complete search history.

(56) References Cited
U.S. PATENT DOCUMENTS
4,188,120 A * 2/1980 McDonald et al. .......... 356/318

| | | | |
|---|---|---|---|
| 5,112,127 A | 5/1992 | Carrabba et al. | |
| 5,880,465 A | 3/1999 | Boettner et al. | |
| 6,128,077 A * | 10/2000 | Jovin et al. ................. | 356/310 |
| 6,483,581 B1 | 11/2002 | Ben-Amotz et al. | |
| 6,750,963 B2 * | 6/2004 | Sampas ...................... | 356/318 |
| 6,809,812 B2 | 10/2004 | Yin | |
| 6,870,612 B2 | 3/2005 | Jiang | |
| 2003/0068638 A1 * | 4/2003 | Cork et al. ...................... | 435/6 |
| 2005/0248758 A1 * | 11/2005 | Carron et al. ............... | 356/301 |
| 2006/0072102 A1 * | 4/2006 | Jianping et al. ............ | 356/28.5 |
| 2008/0174777 A1 * | 7/2008 | Carron ........................ | 356/328 |

FOREIGN PATENT DOCUMENTS
WO 9901750 1/1999

* cited by examiner

Primary Examiner—Tarifur Chowdhury
Assistant Examiner—Abdullahi Nur
(74) Attorney, Agent, or Firm—Joseph J. Christian

(57) ABSTRACT

A system and method for managing optical power for controlling thermal alteration of a sample undergoing spectroscopic analysis is provided. The system includes a moveable laser beam generator for irradiating the sample and a beam shaping device for moving and shaping the laser beam to prevent thermal overload or build up in the sample. The moveable laser beam generator includes at least one beam shaping device selected from the group consisting of at least one optical lens, at least one optical diffractor, at least one optical path difference modulator, at least one moveable mirror, at least one Micro-Electro-Mechanical Systems (MEMS) integrated circuit (IC), and/or a liquid droplet. The system also includes an at least two degree of freedom (2 DOF) moveable substrate platform and a controller for controlling the laser beam generator and the substrate platform, and for analyzing light reflected from the sample.

25 Claims, 12 Drawing Sheets

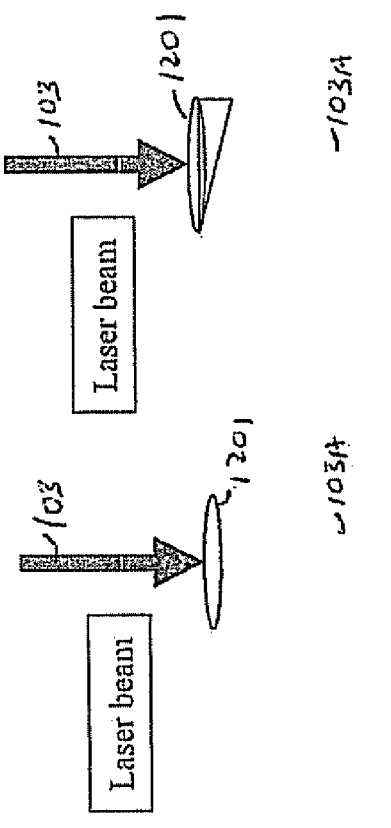
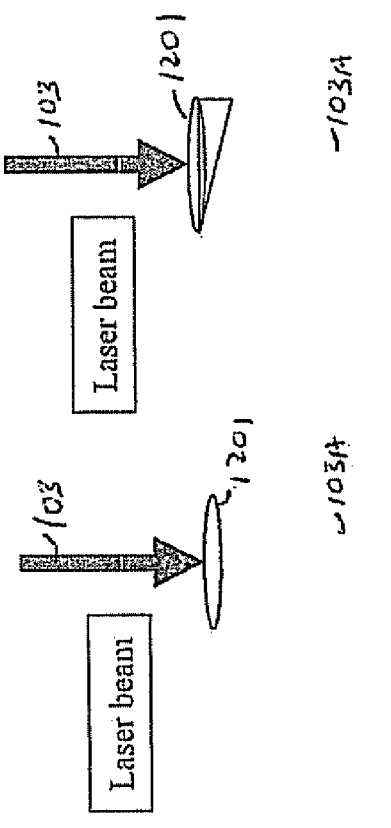
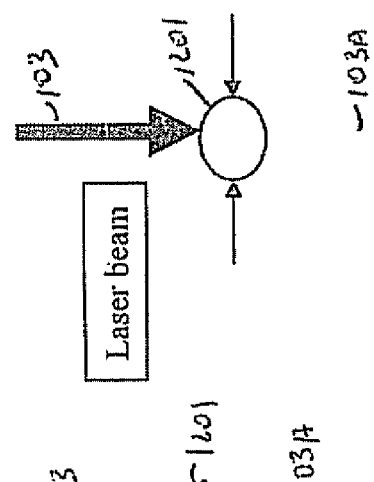
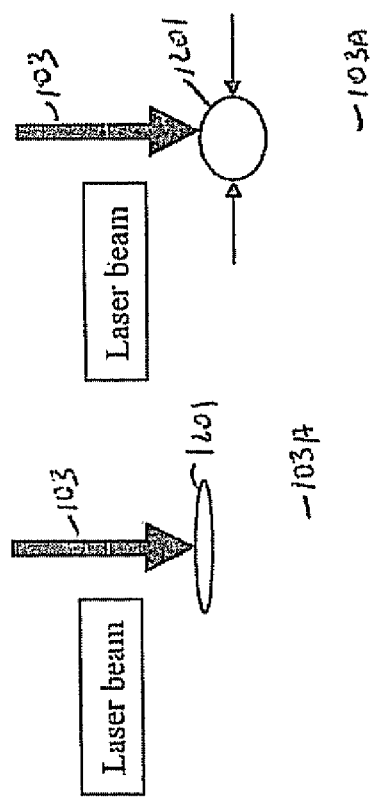
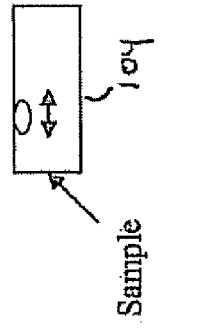
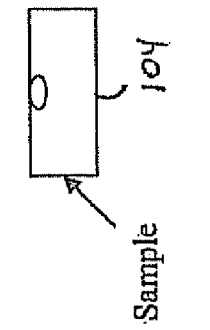
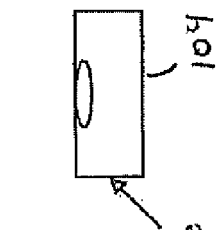
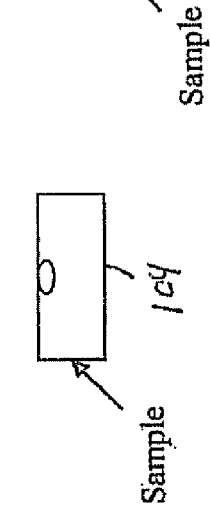
FIG. 12A  FIG. 12B  FIG. 12C  FIG. 12D

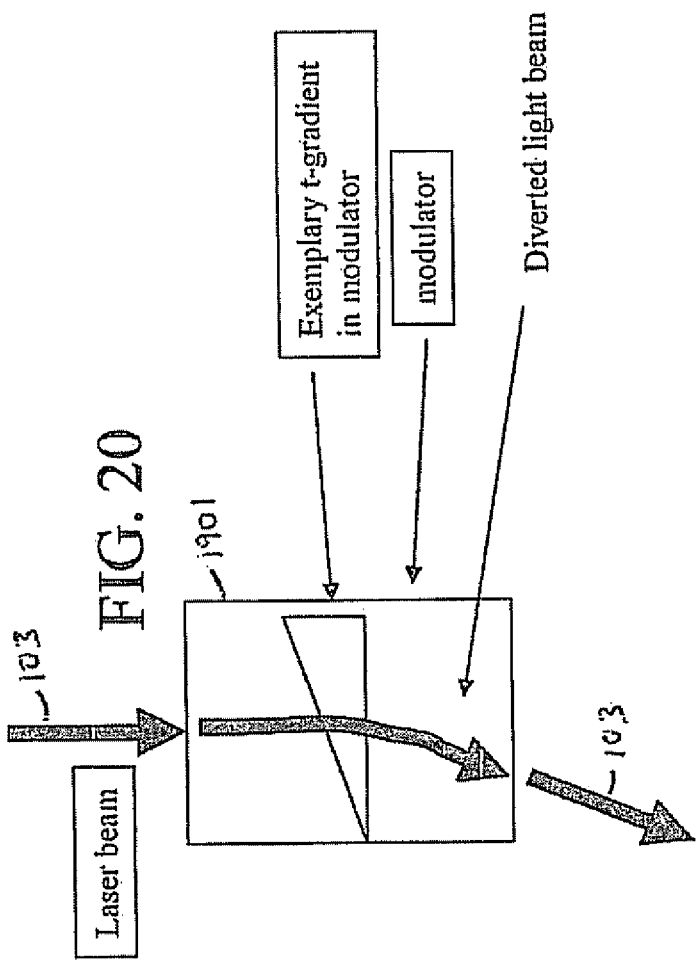
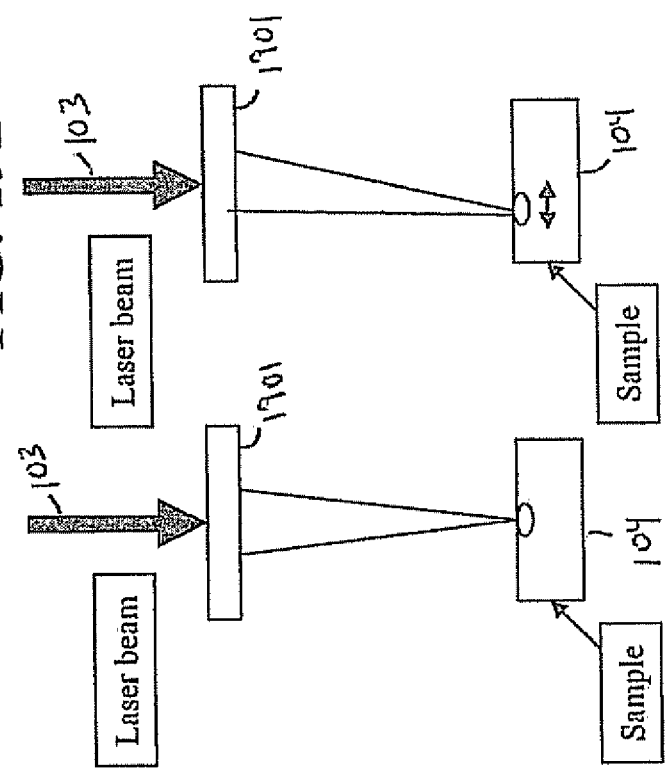

SYSTEM AND METHOD FOR OPTICAL POWER MANAGEMENT

BACKGROUND OF THE INVENTION

1. Field of the Invention

The teachings herein relate to limiting power density induced by a laser and a corresponding temperature increase in a sample interrogated by the laser.

The invention generally relates to spectral analysis systems, more particularly, the invention particularly relates to improvements in Raman systems to permit effective and rapid sample identification.

2. Description of the Related Art

Due to the strong optical absorption in some solids, most of the signal needed to perform a spectroscopic identification is absorbed by the sample and thus unavailable for detection. At the same time, absorption may also lead to a significant thermal change such as a rapid heating, melting and even burning of the sample during the identification process. Absorption may also lead to detonation of some explosive samples.

Thus, not only are the signal levels from the samples very small, but also these weak signals, particularly Raman signals, may be further obscured by large interfering backgrounds due to the fluorescence from thermally induced changes in the sample.

For example, white plastics can be easily and rapidly identified in 0.1 seconds with a Raman spectrometer, such as that disclosed in International Publication WO 99/01750, using a 1 Watt diode laser power, while black plastics cannot be identified under the same conditions due to laser induced detrimental changes.

In order to avoid laser induced detrimental changes in the plastic, it is necessary to decrease the laser power density on the surface of the sample. One way to reduce laser power density is to reduce total laser power that illuminates the surface of the black plastic. But at the same time, to accumulate enough signal for identification the signal collection time has to be increased proportionally. Obviously, this is not acceptable for rapid identification.

Another way to reduce the power density of the laser beam is to increase the size of the laser spot that illuminates the surface of the plastic, while still maintaining a sufficiently high laser power of 1 Watt to allow rapid identification. Experiments have shown that to avoid laser induced detrimental changes in black plastic samples, in the case of 1 Watt total laser power at wavelength 800 nm, the size of the laser spot illuminating the surface of a black plastic sample needs to be increased 40 times, to a size that is greater than 3 mm in diameter to avoid adverse impact on the sample. As a consequence, the signal acceptance area of the collection fiber bundle and the acceptance area of the spectrograph (slit-height times slit-width) must also be increased 40 times.

It will be appreciated that increasing the signal acceptance area of a collection fiber bundle by a factor of 40 is difficult, if not impossible, to achieve from a technical point of view. Enlarging the laser spot size without changing the optical train and components would cause the signal from the sample to overfill the collection fiber bundle and thus decrease the collected signal intensity.

Thus, there exists a need for a quick yet effective method to identify materials using spectral analysis, particularly Raman spectroscopy without damaging the samples.

BRIEF DESCRIPTION OF THE INVENTION

In accordance with one embodiment of the invention a system for managing optical power for controlling thermal alteration of a sample undergoing spectroscopic analysis is provided. The system includes a moveable laser beam generator for irradiating the sample and a beam shaping device for moving and shaping the laser beam to prevent thermal overload or build up in the sample. The system also includes a moveable substrate platform and a controller/analyzer for controlling the laser beam generator, the substrate platform, and for analyzing light reflected from the sample.

In accordance with another embodiment of the invention a method for managing optical power for controlling thermal alteration of a sample undergoing spectroscopic analysis is provided. The method includes selecting a predetermined substrate movement pattern and selecting a predetermined beam movement pattern. The method also includes controlling laser beam dynamics by determining beam power duty cycle and selecting beam diameter change rate. In addition the method, after selecting the substrate material, irradiates and analyzes electromagnetic energy reflected from the sample.

Embodiments of the invention are also directed towards a system for managing optical power for controlling thermal alteration of a sample undergoing Raman spectroscopic analysis. The system includes at least two degrees of freedom (2 DOF) moveable laser beam generator for irradiating the sample. The moveable laser beam generator includes a beam shaping device selected from the group consisting of at least one optical lens, at least one optical diffractor, at least one optical path difference modulator, at least one moveable mirror, at least one Micro-Electro-Mechanical Systems (MEMS) integrated circuit (IC), and/or a liquid droplet. The system also includes at least two degrees of freedom (2 DOF) moveable substrate platform and a controller for controlling the laser beam generator and the substrate platform.

BRIEF DESCRIPTION OF THE DRAWINGS

FIGS. 12A-12D are diagrams showing use of a deformable lens to change beam focal length in accordance with the optical power management system shown in FIG. 1 and the method shown in FIG. 2.

FIGS. 19A-19B illustrate using beam steering using heated glass or polymer to move light or change temperature gradient for induced refractive index gradient in accordance with the optical power management system shown in FIG. 1 and the method shown in FIG. 2.

FIG. 20, shows changing temperature gradient and resulting beam steering in accordance with the optical power management system.

DETAILED DESCRIPTION OF THE INVENTION

Figure 1:
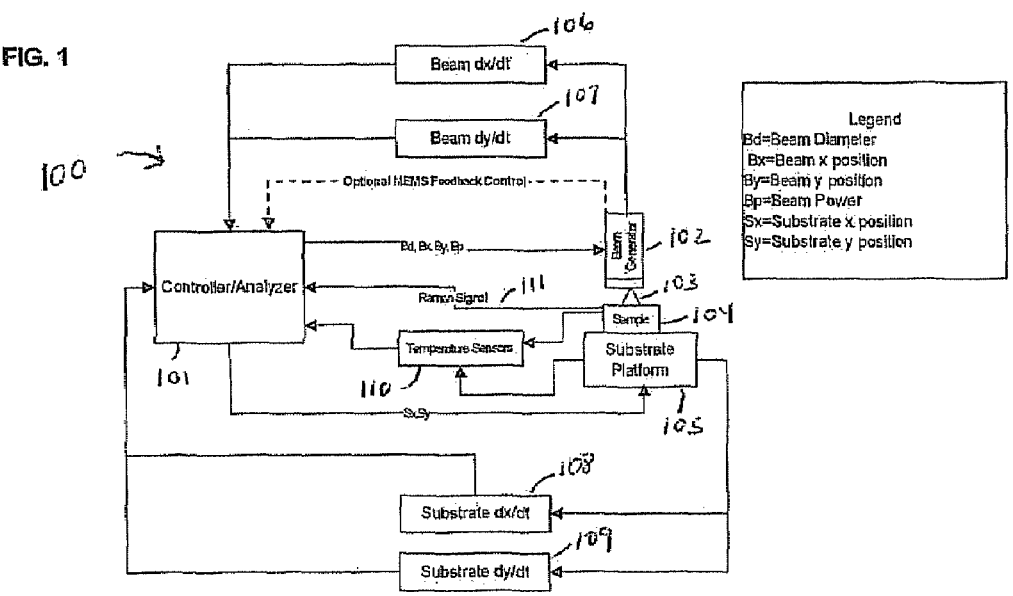
FIG. 1 is a high level system architecture of the optical power management system in accordance with an embodiment of the invention.

Referring to FIG. 1 there is shown a high level system architecture of the optical power management system 100 in accordance with an embodiment of the invention. The optical power management system includes a controller/analyzer 101 for generating beam control signals: beam power (bp); beam x-position (bx); beam y-position (by); and beam diameter (bd). The beam control signals are provided to beam generator 102. Using the beam control signals the beam generator 102 initiates a laser beam 103 incident on sample 104. Various beam control mechanisms in accordance with embodiments of the invention will be discussed herein. It will be understood that the sample 104 may be any suitable sample, such as a solid or liquid sample; or any suitable sample in a condensed phase, for example, gels, pastes, and other forms that may be construed as neither a solid nor a liquid.

Controller/analyzer 101 also generates substrate control signals: substrate-x position and substrate-y position. The substrate control signals are provided to substrate 105. Substrate 105 may be any suitable stationary or moveable substrate for holding the sample 104 to be analyzed. For example, in one embodiment the substrate 105 may be a heat conductive material and/or a cooled substrate in order to reduce heat buildup in the sample 104 resulting from laser beam 103. In another embodiment the substrate 105 may be a spinning substrate bringing the sample 104 within the laser beam 103 according to a fixed periodic rate. It will also be understood that the substrate 105 revolutions may be controlled (increased or decreased) by the controller/analyzer 101 as necessary to prevent excessive temperature build up in sample 104. It will be further understood that substrate 105 may have at least two or more degrees of freedom. For example, the substrate 105 may be able to move in an x, y, or z direction in a Cartesian coordinate system. It will also be understood that the substrate 105 may be moved to effectively move the sample 104 in or out of the focal plane of the laser beam 103.

Controller/analyzer 101 also receives input from Beam dx/dt differentiator 106 which determines velocity of the laser beam 103 in the x-direction. Controller/analyzer 101 also receives input from Beam dy/dt differentiator 107 for determining velocity of the laser beam 103 in the y-direction.

Similarly controller/analyzer 101 receives input from Substrate dx/dt differentiator 108 which determines velocity of the substrate 105 in the x-direction. Controller/analyzer 101 also receives input from Substrate dy/dt differentiator 109 for determining velocity of the substrate 105 in the y-direction.

Controller/analyzer 101 also receives input from temperature sensors 110 for determining temperatures of the sample 104 and/or the temperatures of the substrate 105. It will be appreciated that temperatures of the sample 104 and/or temperatures of the substrate 105 may be temperature gradient profiles of either the sample 104 or the substrate 105. It will be further appreciated that temperature profiles may be used by the controller/analyzer 101 to optimize repositioning of the substrate 105 holding the sample 104 and the laser beam 103 positioning (bx,by) and laser beam 103 diameter (bd) irradiating the sample 104. It will also be appreciated that temperature sensors 110 may also provide characteristic sample data prior to resulting from a low level laser probing beam generated by the beam generator 102.

Controller/analyzer 101 receives and analyzes Raman signals 111 from the sample 104 resulting from beam generator 102 generating laser beam 103 onto sample 104. It will be understood that the controller/analyzer 101 may include any suitable spectrometer system. It will also be understood that controller/analyzer 101 and beam generator 102 may be collocated and may include any suitable combination of lens and/or fiber bundles.

Figure 2:
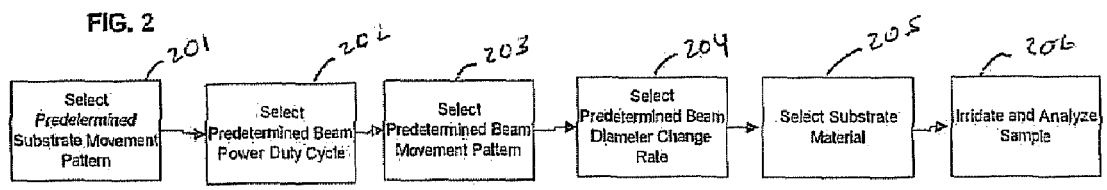
FIG. 2 is a flow chart showing one method for open loop analysis of a sample in accordance with the optical power management system shown in FIG. 1.

Referring also to FIG. 2 there is shown a flow chart showing one method for open loop analysis of a sample in accordance with the embodiment shown in FIG. 1. Controller/analyzer 101 selects a predetermined substrate movement plan 201 for minimizing the amount of time laser beam 103 is incident on any one spot on the sample 104. For example, the predetermined substrate movement plan 201 could be a zig-zag pattern or a circular movement plan.

Figure 14:
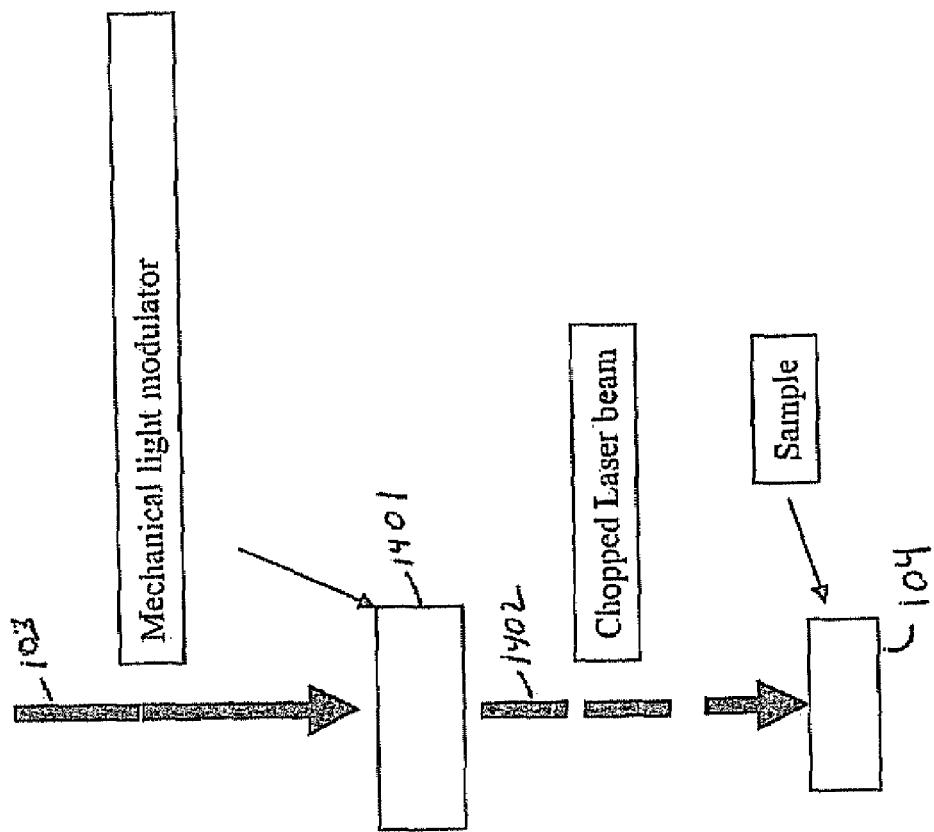
FIG. 14 illustrates the use of mechanical chopping for optical power management in accordance with the optical power management system shown in FIG. 1 and the method shown in FIG. 2.
Figure 13:
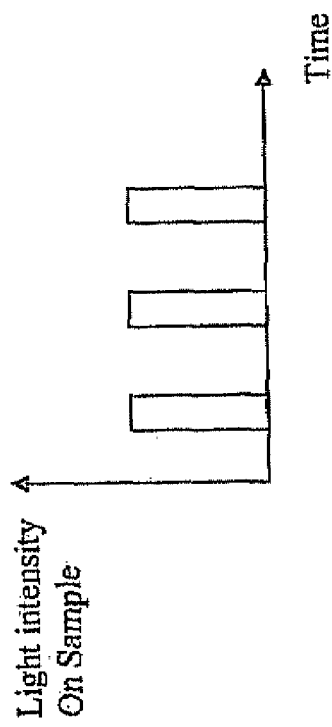
FIG. 13 illustrates the use of electronic chopping for optical power management in accordance with the optical power management system shown in FIG. 1 and the method shown in FIG. 2.

Next, controller/analyzer 101 determines 202 the laser beam 103 duty cycle. In other words, the ratio of laser beam 103 on-sample-time to on-sample-time plus off-sample-time is the laser beam 103 duty cycle. Referring briefly to FIG. 13 and FIG. 14 there are shown two methods of controlling the laser beam 103 duty cycle.

FIG. 13 illustrates chopping for optical power management in accordance with the embodiments shown in FIG. 1 and FIG. 2. In an electronic chopper an electronic signal to the beam generator 102 is electronically modulated (chopped), thus modulating the light intensity as shown in FIG. 13. It will be understood that very short pulses will generate ultrasound in the sample and less energy will be converted into heat, thus resulting in a lower temperature.

FIG. 14 illustrates the use of mechanical chopping for optical power management in accordance with the embodiments shown in FIG. 1 and FIG. 2. The laser beam 103 is modulated (chopped) by mechanical means. Use of a mechanical/optical chopping means, (e.g., with micro-fluidic cooling) is one example. The result is a modulated light beam 1402 reaching the sample 104 and, similar to the electronic chopping described above, short pulses generate ultrasound in sample 104 and less energy will be converted into heat.

Returning to FIG. 1 and FIG. 2, the controller analyzer 101 selects a predetermined beam movement plan 203 for minimizing the amount of time laser beam 103 is incident on any one spot on the sample 104. For example, similar to the substrate movement plan, the predetermined beam movement plan 203 could be a zig-zag pattern or a circular movement plan.

Figures 15A, 15B:
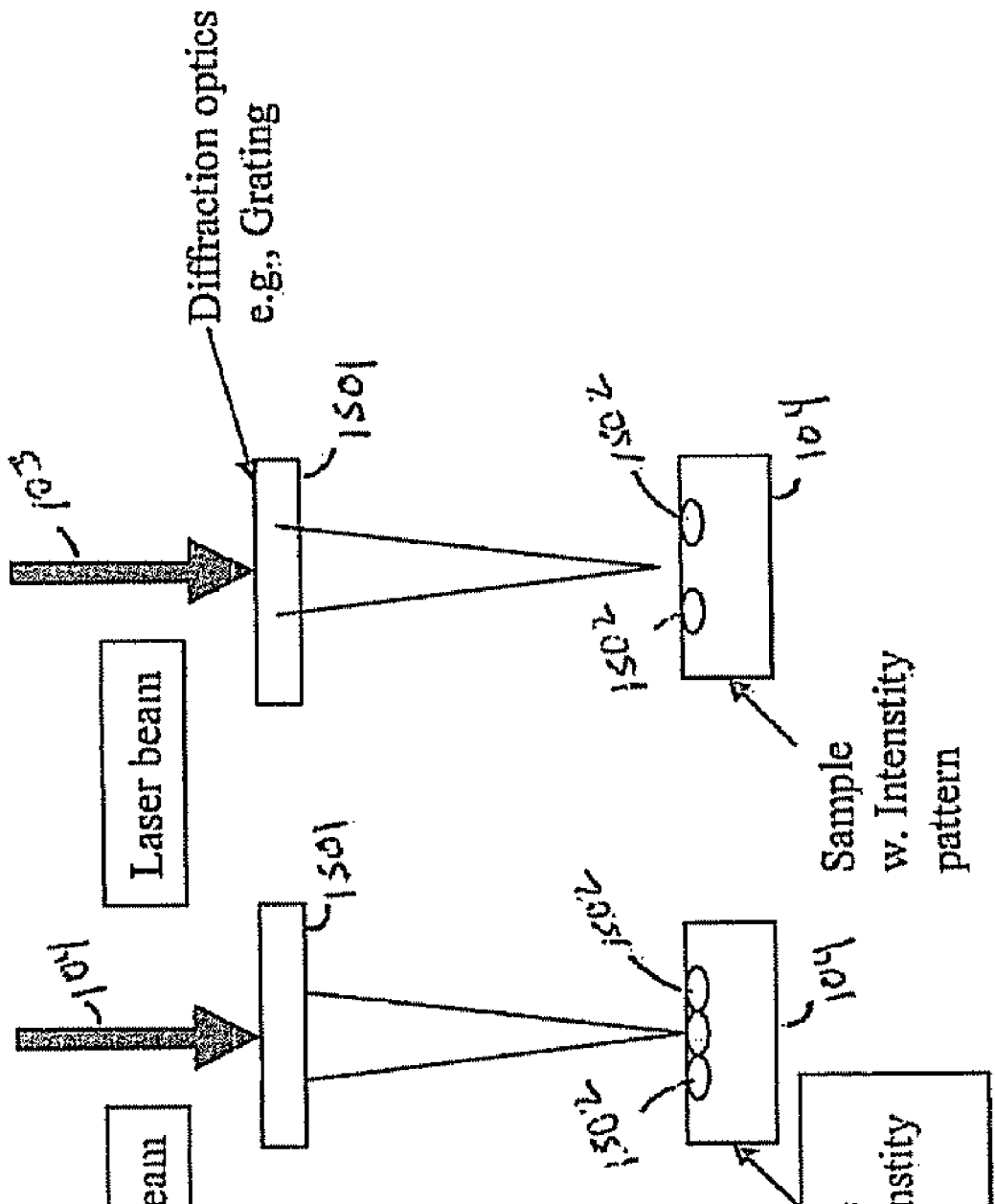
FIGS. 15A-15B illustrate use of an optical grating with variable slit dimension to change the shape of the beam pattern in accordance with the optical power management system shown in FIG. 1 and the method shown in FIG. 2.
Figure 16A:
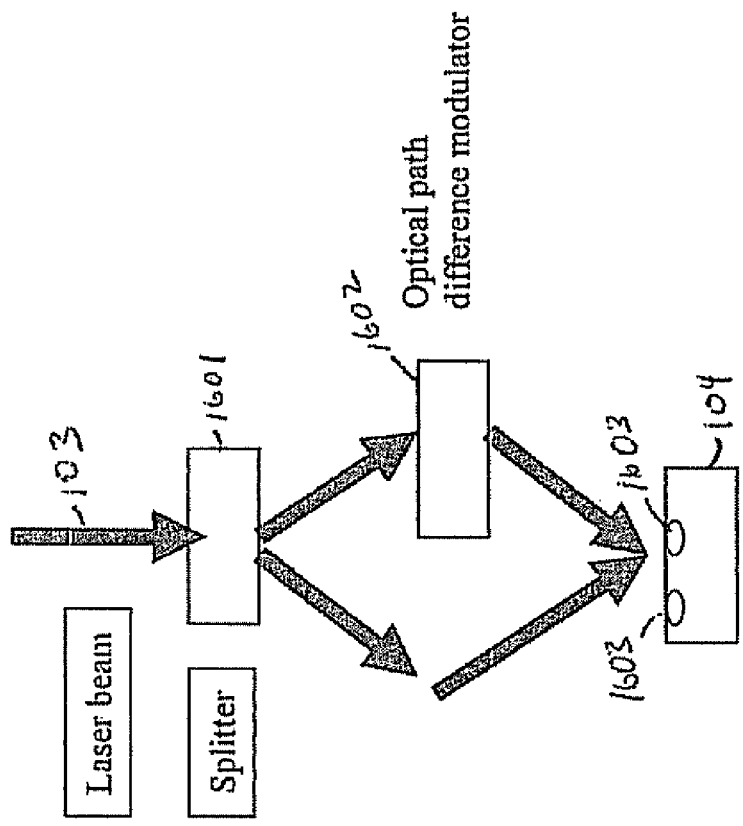
FIGS. 16A-16B illustrate using a split beam and constructive/destructive interference to move beam in accordance with the optical power management systems shown in FIG. 1 and FIG. 2.
Figure 16B:
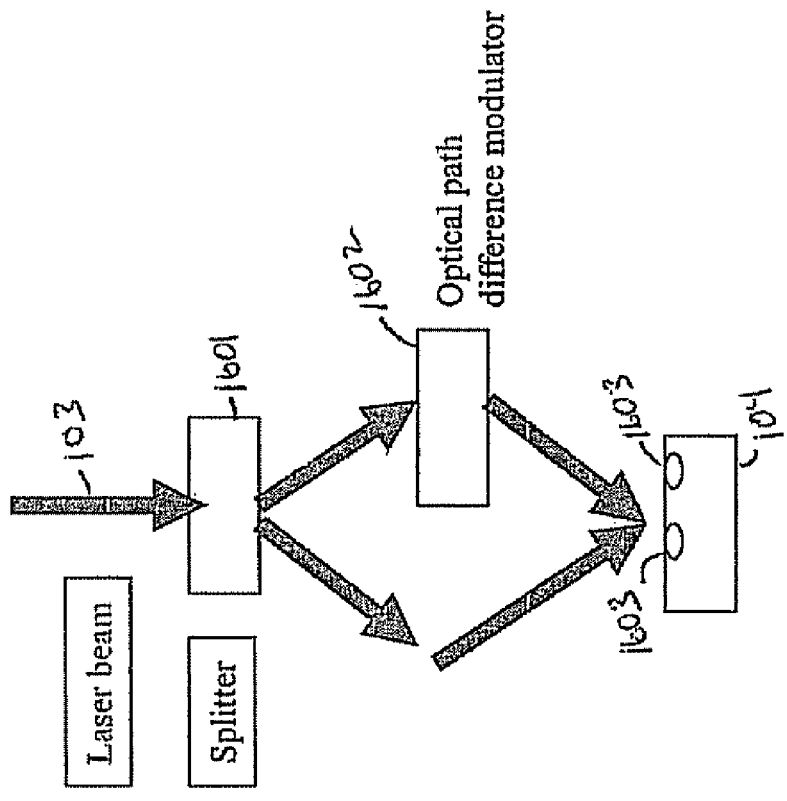
Figure 18B:
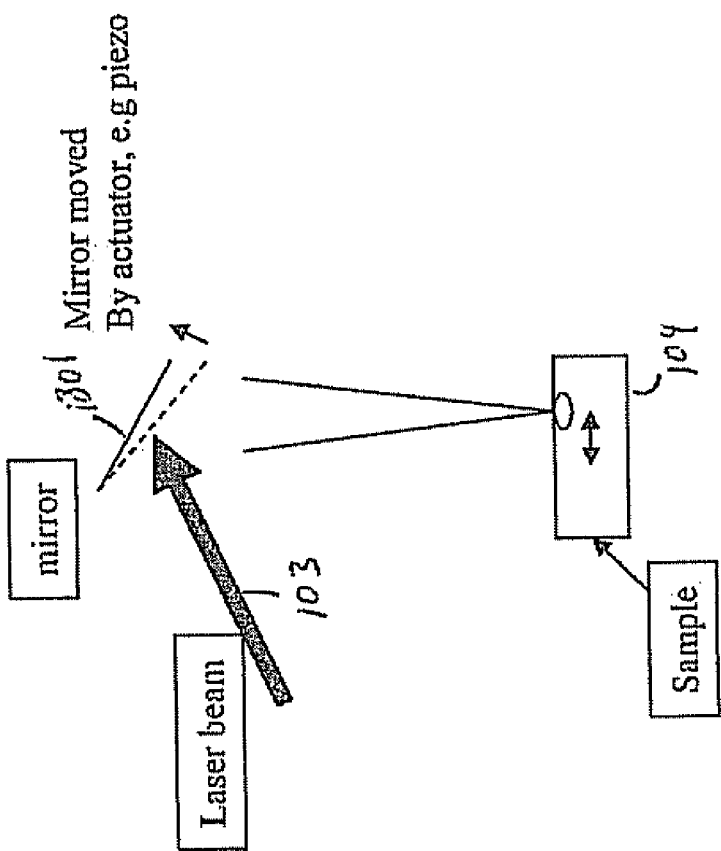
FIGS. 18A-18B illustrate using piezo controlled mirror to move beam in accordance with the optical power management system shown in FIG. 1 and the method shown in FIG. 2.
Figure 18A:
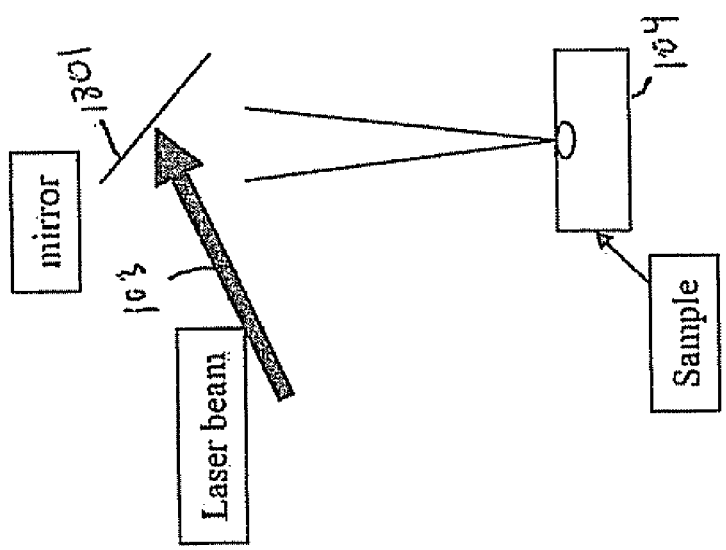

It will be understood that laser beam 103 may be moved by any suitable method. For example, the laser beam 103 may be laterally moved through the use of a rotating glass plate or lens with suitable refraction characteristics. FIGS. 12A-12D are diagrams showing use of a deformable lens 1201 to change beam 103 focal length 103A. In this way the beam 103 is moved away/towards the sample 104 or moved along the sample 104. In addition, lens 1201 may be any suitable converging or schlieren lens. In alternate embodiments, FIGS. 15A-15B illustrate use of an optical grating 1501 with variable slit dimensions to move or change the shape of the beam pattern 1502. It will be appreciated that the grating may be changed by any suitable method necessary to generate a diffractive pattern for moving or shaping the laser beam pattern incident upon the sample 104. In addition, the grating may be generated by acoustic standing waves or by changing the refractive index of air. In another embodiment the beam 103 shape may be moved or changed by splitting the laser beam 103 and changing the optical path length of one of the split beams. FIGS. 16A-16B illustrate using a splitter 1601 to split beam 103 and an optical modulator 1602 for generating constructive/destructive interference patterns 1603 of laser beam 103 incident on sample 104. FIGS. 18A-18B illustrate using piezo controlled mirror 1801 to move beam 103 incident on sample 104. FIGS. 19A-19B illustrate using beam steeling by using heated glass 1901 or polymer to move laser beam 103 or changing the temperature gradient for induced refractive index gradient. This principle is illustrated in FIG. 20 which shows changing temperature gradient and resulting beam steeling.

Figure 21:
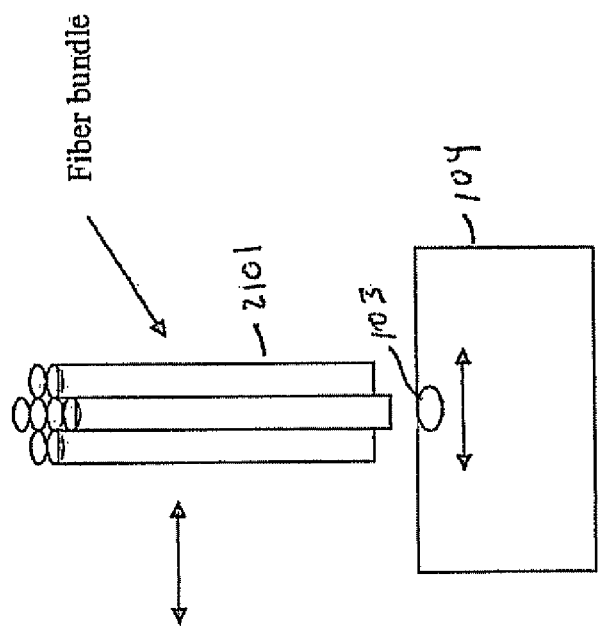
FIG. 21 shows the use of moveable fiber bundles to change beam location for irradiation and signal collection in accordance with the optical power management system shown in FIG. 1 and the method shown in FIG. 2.

In yet another embodiment, FIG. 21 shows the use of moveable fiber bundles 2101 to change beam 103 location on sample 104 for irradiation and signal collection for subsequent analysis. It will be appreciated that any suitable lens or optical collector, e.g., a spherical mirror, telescope, or a zoom lens system may be used.

Figure 4:
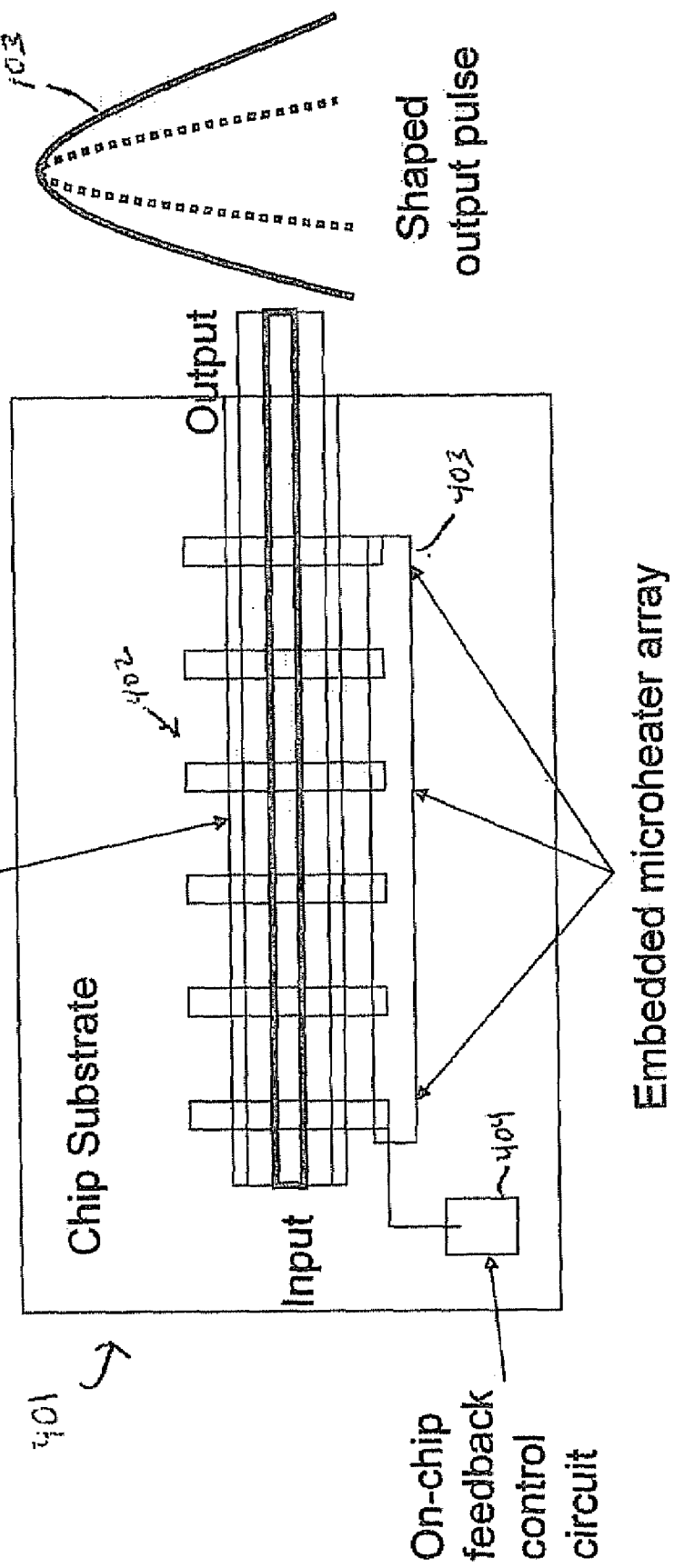
FIG. 4 is a block diagram of a Micro-Electro-Mechanical Systems (MEMS) chip illustrating controlling beam shape in accordance with the optical power management system shown in FIG. 1.
Figure 17:
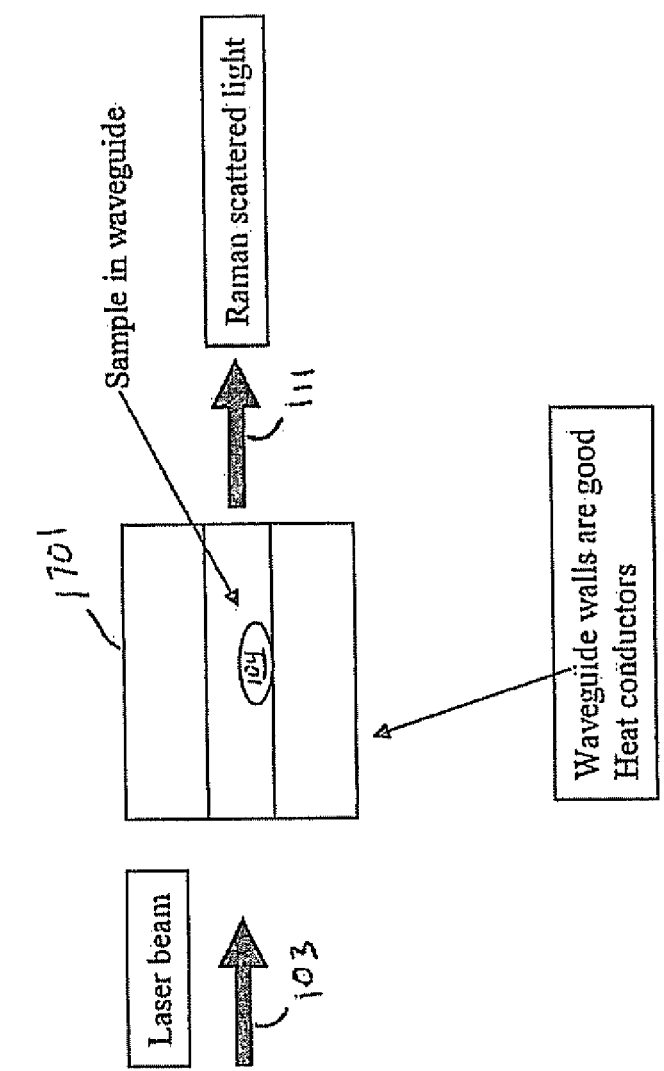
FIG. 17 shows a waveguide and sample for optical power management in accordance with the optical power management system shown in FIG. 1 and the method shown in FIG. 2.

Controller/analyzer 101 also selects, or predetermines, a beam diameter (bd) 204 change rate. For example, in conjunction with the beam and substrate movement plans the controller/analyzer 101 can also vary the diameter size of the laser beam 103 incident on the sample 104. Referring also to FIG. 4 there is shown a block diagram of a MEMS chip 401 illustrating controlling laser beam 103 shape. For example, in order to manage the optical power to excite a Raman signal from the sample 104 under test, the MEMS chip 401 with integrated optical fiber (fiber Bragg grating (FBG) or chirped FBG) 402 may be used. The laser beam 103 power distribution for a given area can be dynamically changed by MEMS chip 401, including embedded micro-heater array 403. The on-chip close-loop circuit 404 can control the laser beam 103 size while monitoring the sample 104 temperature in real time. It will be appreciated that any suitable method for controlling laser beam 103 size and shape may be used. For example a Digital Micro-mirror Device, or DMD chip, may also be used to shape and steer laser beam 103. Referring again to FIG. 2, a suitable substrate 105 is selected according to predetermined characteristics 205. As noted earlier, the substrate may be any suitable substrate such as a suitable heat dissipater or a previously cooled substrate. FIG. 17 shows a waveguide 1701 and sample 104 for optical power management. The waveguide 1701 conducts the laser beam 103 and is also a suitable heat sink to dissipate heat transferred from the sample 104.

Controller/analyzer 101 generates command signals to the beam generator 102 to irradiate and analyze 206 the resulting signals returning from the sample 104.

Figure 3:
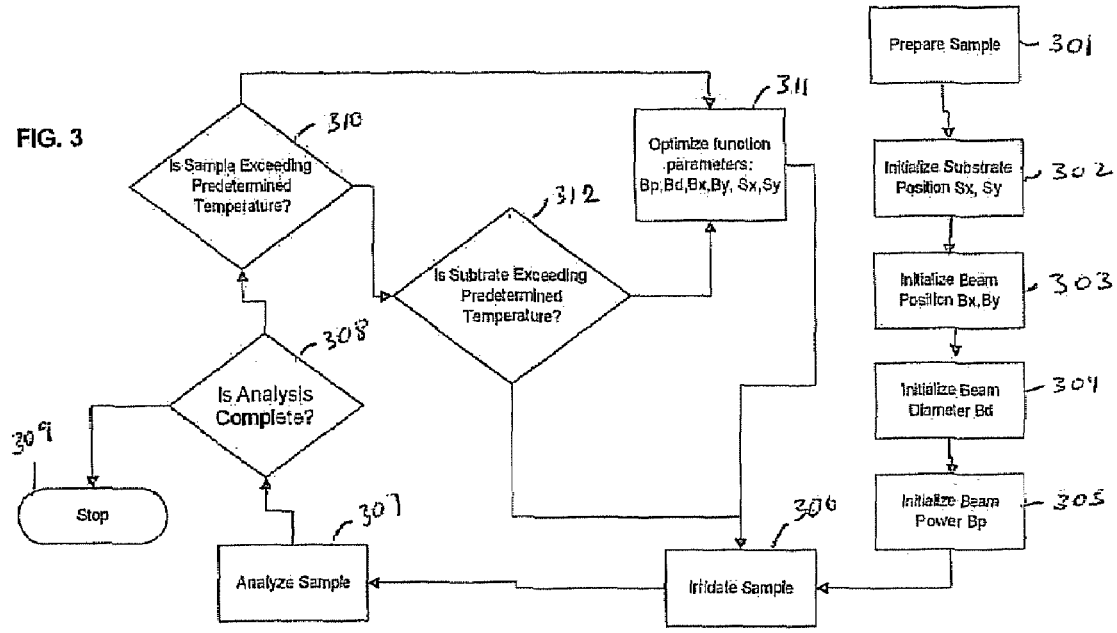
FIG. 3 is a flow chart showing a method for closed loop analysis of a sample in accordance with the optical power management system shown in FIG. 1.

Referring now to FIG. 1 and FIG. 3. FIG. 3 there is shown a flow chart illustrating a method for closed loop analysis of a sample in accordance with the embodiment shown in FIG. 1. A sample 104 is prepared 301 for analysis. As noted earlier, the sample 104 may be positioned or otherwise attached to a suitable substrate 105.

Figure 5:
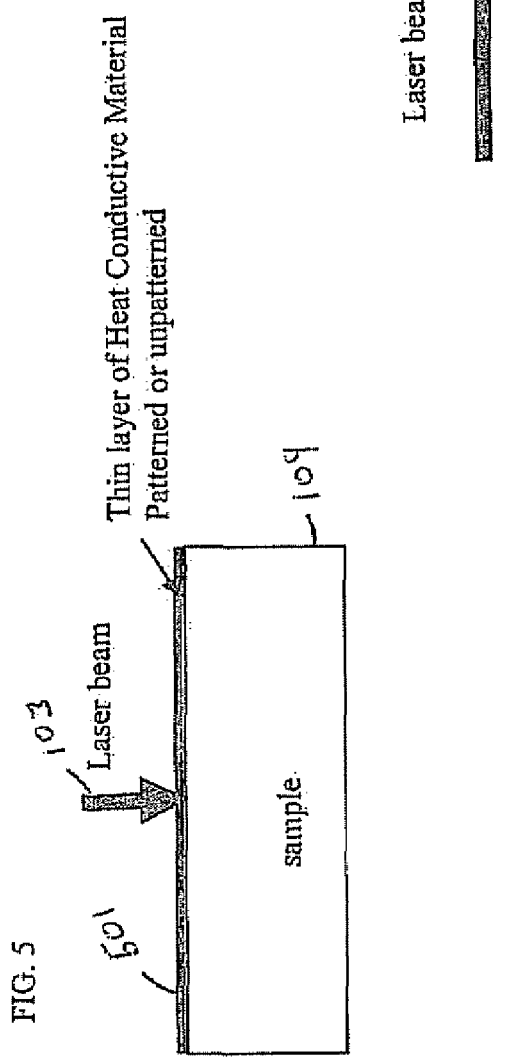
FIG. 5 illustrates placing a thin layer of heat conductive material on a sample in accordance with the optical power management system shown in FIG. 1 and the method shown in FIG. 2.
Figure 6:
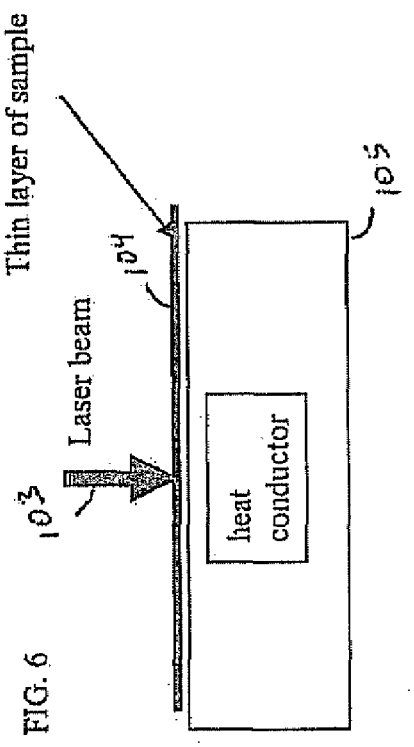
FIG. 6 illustrates placing a thin layer of sample on a heat conductive material in accordance with the optical power management system shown in FIG. 1 and the method shown in FIG. 2.
Figure 8:
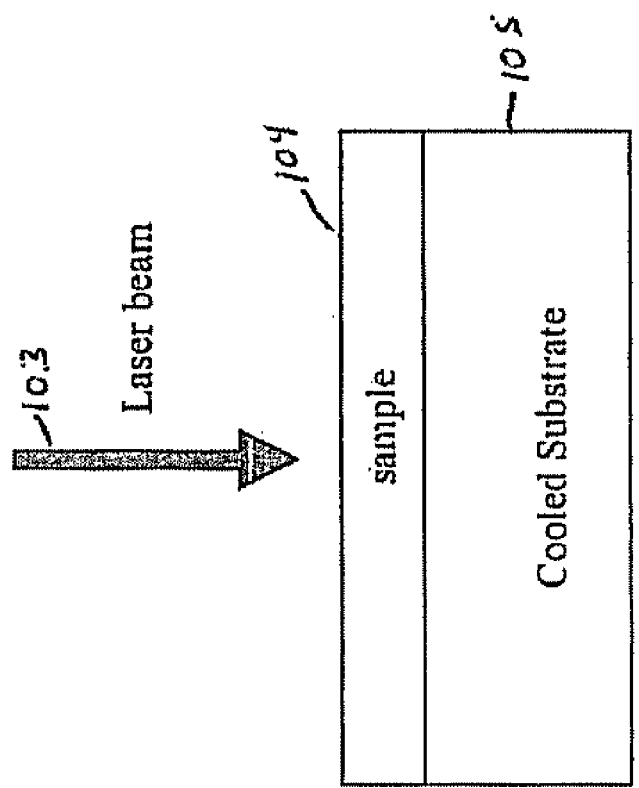
FIG. 8 illustrates snap freezing the sample for optical power management in accordance with the optical power management system shown in FIG. 1 and the method shown in FIG. 2.
Figure 10:
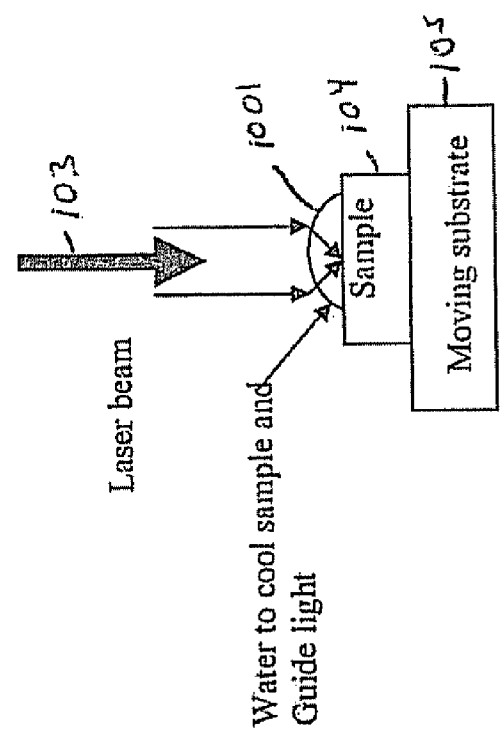
FIG. 10 illustrates placing a water droplet on the sample to cool it and use it as an optical means to focus Raman radiation in accordance with the optical power management system shown in FIG. 1 and the method shown in FIG. 2.

In alternate embodiments a solid sample may be prepared as shown in FIG. 5, FIG. 6, FIG. 8, or FIG. 10. FIG. 5 illustrates placing a thin layer of heat conductive material 501 on the sample 104. FIG. 6 illustrates placing a thin layer of the sample 104 on a heat conductive material substrate 105. FIG. 8 illustrates snap freezing the sample 104 for optical power management (i.e., reduce sample heat). FIG. 10 illustrates placing a droplet 1001 of a liquid transparent to the light source on the sample 104 to cool the sample 104, and also use the droplet as an optical means to focus the laser beam 103. By changing the droplet geometry using electro wetting or thermo wetting techniques the droplet behaves like a lens with a tunable focal length which enables us to vary the optical power density at the surface of the sample. In addition, the sample may be coated with optical dyes to enhance spectral analysis.

Figure 7:
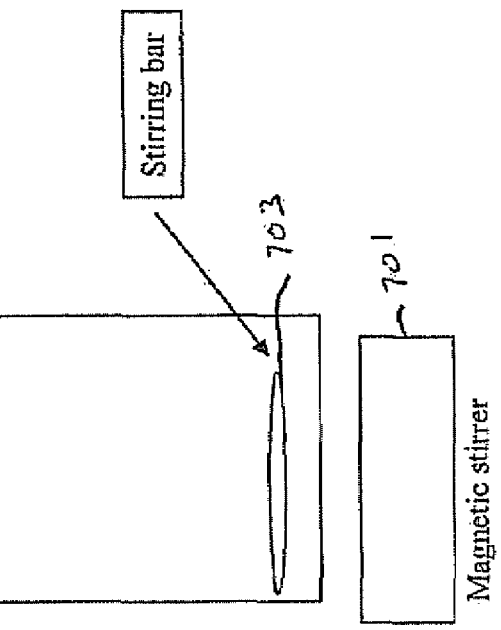
FIG. 7 illustrates a magnetic stirrer for mixing a liquid sample in accordance with the optical power management system shown in FIG. 1 and the method shown in FIG. 2.
Figure 9:
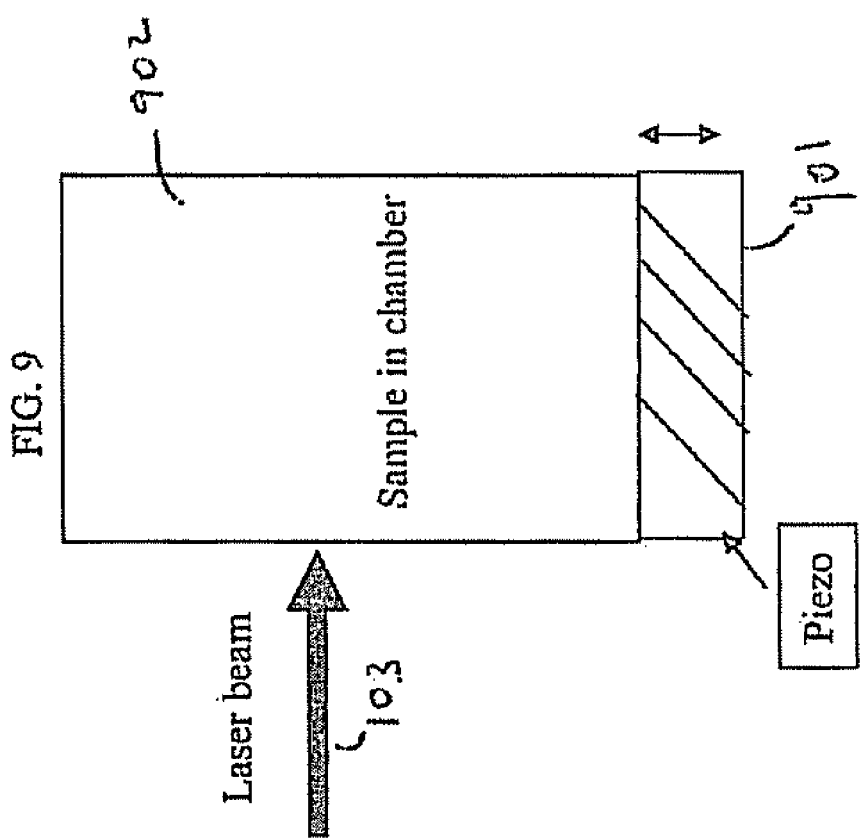
FIG. 9 illustrates a piezo stirrer for moving a liquid or solid sample in accordance with the optical power management system shown in FIG. 1 and the method shown in FIG. 2.
Figure 11:
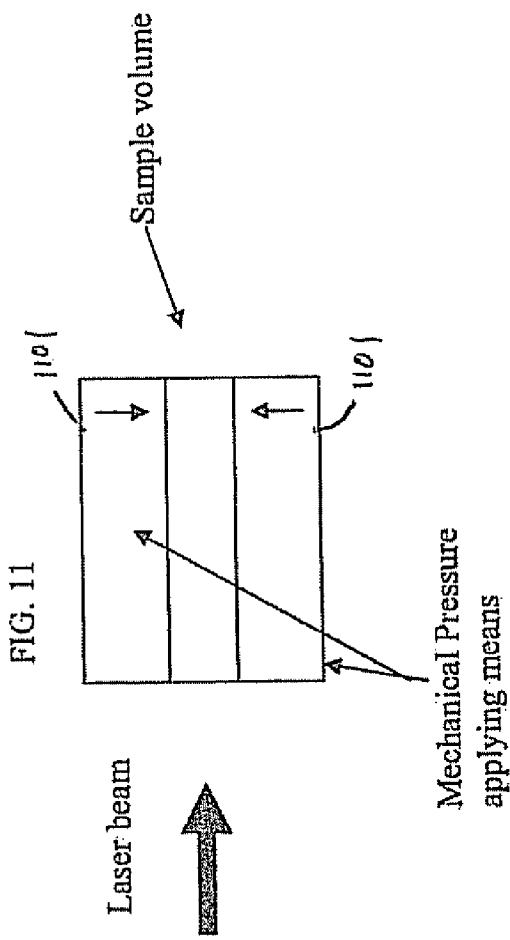
FIG. 11 illustrates compressing a sample to increase the sample density, and thus the signal and thermal diffusivity in accordance with the optical power management system shown in FIG. 1 and the method shown in FIG. 2.

In yet more alternate embodiments a liquid sample may be prepared as shown in FIG. 7, FIG. 8, FIG. 9, or FIG. 11. FIG. 7 illustrates a magnetic stirrer 701 for mixing a liquid sample 702. The liquid sample 702 is stirred with stirring bar 703 so that new fluid is exposed to the laser light and heating is reduced. FIG. 8 again illustrates snap freezing the sample 104 for optical power management. FIG. 9 illustrates a piezo stirrer 901 for moving a liquid or solid sample 902. FIG. 11 illustrates compressing sample 104. Compressing the sample 104 volume by applying mechanical pressure which results in an increase in sample 104 density and a corresponding increased Raman cross-section and better heat conductivity.

It will be understood that any of the sample preparations described herein may be used independently or in conjunction with each other or other suitable sample preparations that will allow the sample 104 to be analyzed without destructive irradiation.

Referring again to FIG. 3 and FIG. 1, the controller/analyzer 101 positions 302 the substrate 105 according to a predetermined x-y position. It will also be understood that the controller/analyzer 101 may dynamically position the substrate according to sample 104 size and selected beam movement plan discussed earlier. Similarly, controller/analyzer 101 positions 303 beam generator 102 according to a predetermined x-y position. It will again be understood that the controller/analyzer 101 may dynamically position the beam generator 102 according to sample 104 size and selected beam movement plan discussed earlier. The controller/analyzer 101 initializes 304 laser beam 103 diameter in accordance with a predetermined beam diameter plan 203 to reduce power density and resulting generated heat within the sample 104. It will be further understood that beam generator 102 may have at least two or more degrees of freedom. For example, beam generator 102 may be able to move in an x, y, or z direction in a Cartesian coordinate system. It will also be understood that the beam generator 102 may be moved to effectively move the sample 104 in or out of the focal plane of the laser beam 103.

Beam power is initialized 305 by the beam generator 102 in accordance with predetermined data or dynamically derived data. For example, sample 104 may be irradiated with a low level laser beam 103 to determine sample characteristics such as sample melting point, reflectance qualities, or detect evaporating molecules as an early indicator for sample degradation. The sample 104 is illuminated for a predetermined time span and properties of the sample, e.g., temperature increase, reflectivity are detected. The material property information is then used by controller/analyzer 101 to maximize the output power for the laser beam 103 so that the sample 104 critical temperature is not exceeded. Still referring to FIG. 3 and FIG. 1, the sample 104 is irradiated 306 by beam generator 102 and reflected signal is analyzed 307 by controller/analyzer 101. If the analysis is complete 308 the method process stops 309. Otherwise, the controller/analyzer 101 determines 310 if the sample 104 is exceeding, or will exceed, predetermined criteria, (e.g., a temperature threshold). If the sample 104 predetermined temperature threshold is exceeded, or will be exceeded, under the function parameter set, (e.g., beam position, beam velocity, and beam power), the controller/analyzer 101 optimizes 311 function parameters Bp, Bd, Bx, By, Sx, Sy to minimize sample 104 temperature and/or projected sample temperature. It will be understood that the function parameters may also be in other coordinates such as polar or rotational coordinates to accommodate rotational substrates. Similarly, the controller/analyzer 101 determines 312 if the substrate 105 is exceeding, or will exceed, predetermined criteria, e.g., a temperature threshold or temperature gradient. If the substrate 105 predetermined temperature threshold is exceeded, or will be exceeded, under the function parameter set, e.g., beam position, beam velocity, and beam power, the controller/analyzer 101 optimizes 311 function parameters Bp, Bd, Bx, By, Sx, Sy to minimize the substrate 105 temperature threshold and/or temperature gradient. The controller/analyzer 101 then continues to irradiate 306 the sample 104 until the sample 104 is analyzed or a predetermined time span has been exceeded (not shown).

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, and is generally described by the appended claims.

What is claimed as new and desired to be protected by Letters Patent of the United States is:

1. A system for managing optical power for controlling thermal alteration of a sample undergoing Raman spectroscopic analysis, the system comprising:
   a moveable laser beam generator for irradiating the sample, wherein the moveable laser beam generator comprises:
   at least one beam shaping device, wherein the at least one beam shaping device comprises at least one Micro-Electro-Mechanical Systems (MEMS) integrated circuit (IC);
   a moveable substrate platform; and
   a controller/analyzer for controlling the laser beam generator, the substrate platform, and for analyzing light reflected from the sample;
   wherein the MEMS IC comprises:
   at least one optical input;
   at least one optical output optically connected to the at least one optical input;
   at least one fiber Bragg grating disposed between the at least one optical input and the at least one optical output;
   a microheater array for adjusting the at least one fiber Bragg grating optical Properties; and
   a feedback control circuit connected to the microheater array, and wherein the feedback control circuit is connectable to the controller/analyzer.

2. The system as in claim 1 further comprising at least one moveable substrate platform differentiator connectable to the moveable substrate platform.

3. The system as in claim 2 wherein the at least one moveable substrate platform differentiator comprises:
   a substrate dx/dt differentiator for measuring velocity of the moveable substrate platform along an x-axis; and
   a substrate dy/dt differentiator for measuring velocity of the moveable substrate platform along a y-axis, perpendicular to the x-axis.

4. The system as in claim 1 further comprising at least one moveable laser beam generator differentiator connectable to the moveable substrate platform.

5. The system as in claim 4 wherein the at least one moveable laser beam generator differentiator comprises:
   a laser beam generator dx/dt differentiator for measuring velocity of the moveable laser beam generator along the x-axis; and
   a laser beam generator dy/dt differentiator for measuring velocity of the moveable laser beam generator along the y-axis, perpendicular to the x-axis.

6. The system as in claim 1 wherein the at least one beam shaping device is disposed between the moveable laser beam generator and the sample.

7. The system as in claim 1 wherein the MEMS IC further comprises at least one chirped fiber Bragg grating disposed between the at least one optical input and the at least one optical output.

8. The system as in claim 1 wherein the moveable laser beam generator comprises a moveable plurality of optical fibers bundled collimated along a common axis.

9. The system as in claim 1 wherein the moveable laser beam generator comprises at least one actuator controlled mirror.

10. The system as in claim 1 wherein the moveable laser beam generator comprises an electronic modulator.

11. The system as in claim 1 wherein the moveable laser beam generator comprises a mechanical modulator.

12. The system as in claim 1 wherein the moveable substrate platform comprises a heat conductor.

13. The system as in claim 1 wherein the moveable substrate platform comprises at least one piezo actuator.

14. The system as in claim 1 wherein the moveable substrate platform comprises a plurality of bearing surfaces adaptable to applying mechanical pressure to the sample.

15. The system as in claim 1 wherein the moveable substrate platform comprises a optical waveguide.

16. A method for managing optical power for controlling thermal alteration of a sample undergoing Raman spectroscopic analysis, the method comprising:
   selecting a predetermined substrate movement pattern;
   selecting a predetermined beam movement pattern;
   determining beam power duty cycle;
   selecting beam diameter change rate;
   selecting substrate material;
   irradiating the sample;
   monitoring at least one temperature;
   determining if the at least one temperature is exceeding at least one predetermined threshold; and
   optimizing at least one of beam movement pattern, substrate movement pattern, beam movement velocity, substrate movement velocity, and beam diameter change rate; and
   analyzing electromagnetic energy reflected from the sample.

17. The method as in claim 16 further comprising preparing the sample, wherein preparing the sample comprises cooling the sample.

18. The method as in claim 16 further comprising preparing the sample, wherein preparing the sample comprises stirring the sample.

19. The method as in claim 16 wherein selecting the predetermined substrate movement pattern further comprises initiating the predetermined substrate pattern from predetermined substrate coordinates.

20. The method as in claim 16 wherein selecting the predetermined beam movement pattern further comprises initiating the predetermined beam movement pattern from predetermined beam position coordinates.

21. The method as in claim 16 wherein monitoring at least one temperature comprises monitoring a sample temperature change rate.

22. The method as in claim 16 wherein monitoring the at least one temperature comprises monitoring a substrate temperature change rate.

23. A system for managing optical power for controlling thermal alteration of a sample undergoing Raman spectroscopic analysis, the system comprising:
   a moveable laser beam generator for irradiating the sample, wherein the moveable laser beam generator comprises:
   at least one beam shaping device, wherein the at least one beam shaping device comprises at least one Micro-Electro-Mechanical Systems (MEMS) integrated circuit (IC);
   a moveable substrate platform;
   a controller/analyzer for controlling the laser beam generator, the substrate platform, and for analyzing light reflected from the sample;
   at least one optical splitter; and
   at least one optical path difference modulator optically connectable to the at least one optical splitter.

24. A system for managing optical power for controlling thermal alteration of a sample undergoing Raman spectroscopic analysis, the system comprising:
   a moveable laser beam generator for irradiating the sample, wherein the moveable laser beam generator comprises:
   at least one beam shaping device, wherein the at least one beam shaping device comprises at least one Micro-Electro-Mechanical Systems (MEMS) integrated circuit (IC);
   a moveable substrate platform, wherein the moveable substrate platform comprises:
      at least one magnetic stirring device; and
      at least one moveable magnet, wherein the at least one moveable magnet is magnetically connectable to the at least one magnetic stirring device; and
   a controller/analyzer for controlling the laser beam generator, the substrate platform, and for analyzing light reflected from the sample.

25. A system for managing optical power for controlling thermal alteration of a sample undergoing Raman spectroscopic analysis, the system comprising:
   a moveable laser beam generator for irradiating the sample, wherein the moveable laser beam generator comprises:
   at least one beam shaping device, wherein the at least one beam shaping device comprises at least one Micro-Electro-Mechanical Systems (MEMS) integrated circuit (IC);
   a moveable substrate platform, wherein the moveable substrate platform comprises a plurality of bearing surfaces adaptable to applying mechanical pressure to the sample; and
   a controller/analyzer for controlling the laser beam generator, the substrate platform, and for analyzing light reflected from the sample.

* * * * *

UNITED STATES PATENT AND TRADEMARK OFFICE
CERTIFICATE OF CORRECTION

| | | |
|---|---|---|
| PATENT NO. | : 7,692,785 B2 | |
| APPLICATION NO. | : 11/693277 | |
| DATED | : April 6, 2010 | |
| INVENTOR(S) | : Sutherland et al. | |

It is certified that error appears in the above-identified patent and that said Letters Patent is hereby corrected as shown below:

Title Page, Item (75), "Inventors", delete "Willam" and insert -- William --, therefor.

In Column 5, Line 59, delete "steeling" and insert -- steering --, therefor.

In Column 5, Line 64, delete "steeling." and insert -- steering. --, therefor.

In Column 8, Line 36, in Claim 1, delete "Properties;" and insert -- properties; --, therefor.

Signed and Sealed this

Tenth Day of August, 2010

David J. Kappos
*Director of the United States Patent and Trademark Office*